United States Patent [19]

Gehrer et al.

[11] Patent Number: 5,880,321

[45] Date of Patent: Mar. 9, 1999

[54] PREPARATION OF 1,1-DIPHENYLETHANES

[75] Inventors: Eugen Gehrer; Karsten Eller, both of Ludwigshafen; Günther Effler, Schifferstadt, all of Germany

[73] Assignee: BASF Aktiengesellschaft, Ludwigshafen, Germany

[21] Appl. No.: 46,692

[22] Filed: Mar. 24, 1998

[30] Foreign Application Priority Data

Mar. 27, 1997 [DE] Germany ......................... 197 13 071.2

[51] Int. Cl.$^6$ ............................... C07C 2/66; C07C 1/20
[52] U.S. Cl. ......................... 585/467; 585/469; 585/446
[58] Field of Search ................................... 585/467, 446, 585/469

[56] References Cited

U.S. PATENT DOCUMENTS

| | | | |
|---|---|---|---|
| 3,760,024 | 9/1973 | Cattanach | 260/673 |
| 3,972,983 | 8/1976 | Ciric | 423/318 |
| 4,011,274 | 3/1977 | Watanabe et al. | 260/668 C |
| 5,073,655 | 12/1991 | Angevine et al. | 585/467 |
| 5,098,686 | 3/1992 | Delprato et al. | 423/308 |
| 5,453,555 | 9/1995 | Chang et al | 585/469 |

FOREIGN PATENT DOCUMENTS

| | | |
|---|---|---|
| 195 16 717 | 11/1998 | Germany . |
| 50012064 | 6/1973 | Japan . |
| 50-12064 | of 1975 | Japan . |
| 55-33692 | of 1980 | Japan . |

OTHER PUBLICATIONS

EMT: Internet Search Document, Aug. 1988.
Derwent Abst. DE 195 16 717.

*Primary Examiner*—Glenn Caldarola
*Assistant Examiner*—Thuan D. Dang
*Attorney, Agent, or Firm*—Keil & Weinkauf

[57] ABSTRACT

In a process for preparing unsubstituted or substituted 1,1-diphenylethanes by catalytic reaction of benzene and styrene in the presence of a zeolite catalyst, it being possible for benzene and styrene each independently to have 1 to 5 substituents selected from halogen, $C_{1-10}$-alkyl, $C_{1-10}$-alkoxy, $C_{1-10}$-acyl, $C_{1-10}$-acyloxy or cyano, the zeolite catalyst is of the EMT or ZSM-20 type.

9 Claims, No Drawings

PREPARATION OF 1,1-DIPHENYLETHANES

The preparation of 1,1-diphenylethanes

The invention relates to a process for preparing unsubstituted or substituted 1,1-diphenylethanes and to the use of certain catalysts for their preparation.

Diphenylethane is an important intermediate for preparing diphenylethene, which is used as comonomer for preparing plastics. Diphenylethene can be obtained in good yields by catalytic dehydrogenation of diphenylethane. However, the preparation of diphenylethane by methods customary to date is not entirely satisfactory.

DE-A-195 16 717 describes a process for preparing diarylethanes from unsubstituted or substituted benzene and unsubstituted or substituted styrene. This reaction is carried out in the presence of beta zeolites or mordenites as heterogeneous catalysts. It is possible to react styrene and benzene, but the steady-state styrene concentration must be kept at a minimum for selective alkylation of benzene with styrene to give 1,1-diphenylethane to be possible. The byproduct content increases at higher steady-state styrene concentrations. A large excess of benzene is therefore normally used, resulting in good yields, but there is also considerable effort needed for working up and purifying the 1,1-diphenylethane.

It is an object of the present invention to provide a catalyst for reacting benzene and styrene to give 1,1-diphenylethane, which has higher selectivity than known catalysts and tolerates higher steady-state styrene concentrations without resulting in a larger content of byproducts.

We have found that this object is achieved by using zeolite catalysts of the ZSM-20 and/or EMT types for preparing unsubstituted or substituted 1,1-diphenylethane.

The catalysts are preferably in their H form for this purpose.

The zeolite catalyst of the ZSM-20 type employed according to the invention, and processes for preparing it, are described in U.S. Pat. No. 3,972,983. It is particularly the H forms of the catalysts listed in U.S. Pat. No. 3,972,983 which are employed. Structurally, they are mixed crystals of EMT and Y zeolites.

The EMT zeolites which likewise can be employed according to the invention are described, for example, in EP-A-0 364 352 and FR-A-2 638 444. They are derived from faujasite structures and differ from these by having another linkage sequence. Whereas faujasites, like Y zeolites, have a cubic structure, EMT zeolites have a hexagonal structure. Processes for preparing them, and EMT zeolites which can be used, are described in EP-A- 0 364 352. They can be crystallized with the aid of a template (18-crown-6) from a gel mixture having the composition of, for example, 10 $SiO_2$:1 $Al_2O_3$:2.4 $Na_2O$:1 18-crown-6:130 $H_2O$ at from 80° to 110° C. over the course of 1 to 2 weeks. The crystallization can be speeded up by adding additives such as NaF, oxalic acid and citric acid. It is particularly advantageous to employ large zeolite crystals with diameters of more than 2 $\mu m$ which can be obtained using Aerosil ($SiO_2$) as silicon source. Depending on the crystallization conditions, ZSM-20 zeolites may also be produced in addition to the pure EMT.

The catalysts employed according to the invention can be either suspended in powder form in the reaction mixture or employed as shaped articles, for example in a fixed bed reactor. Any suitable shapes can be employed for this, such as extrudates, tablets, pellets, beads, granules or chips. Processes for producing the shaped articles from the catalysts according to the invention are known.

In the process according to the invention for preparing unsubstituted or substituted 1,1-diphenylethanes by catalytic reaction of benzene and styrene in the presence of a zeolite catalyst of the EMT or ZSM-20 type, benzene and styrene may independently have 1 to 5 substituents selected from halogen, $C_{1-10}$-alkyl, $C_{1-10}$-alkoxy, $C_{1-10}$-acyl, $C_{1-10}$-acyloxy or cyano.

The term "benzene" means in this connection both unsubstituted benzene and substituted benzenes. Likewise, the term "styrene" means unsubstituted styrene and styrenes substituted on the phenyl radical. The vinyl group in substituted styrene preferably has no substituents. The substituents in benzene and styrene are present in any position independently of one another, ie. different substituents may be present at all positions in the molecules. The benzene and styrene employed according to the invention preferably have independently 0 to 3, particularly preferably 0 to 2, in particular 0 to 1, substituents on the aromatic nucleus. Benzene and styrene in unsubstituted form are particularly preferably used.

Suitable substituents are halogen atoms, such as fluorine, chlorine, bromine or iodine atoms. The alkyl, alkoxy, acyl or acyloxy substituents preferably have 1 to 5, particularly preferably 1 to 3, carbon atoms. These radicals preferably have linear aliphatic carbon chains.

It is particularly preferred for the benzene and styrene employed each independently to have a maximum of one substituent, and the substituent in styrene is located in the p position. This substituent can be selected as hereinbefore.

The reaction of benzene and styrene is preferably carried out in liquid phase. In this case, the reaction is preferably carried out at from −20° to 300° C., particularly preferably 10° to 250° C., in particular 50° to 200° C. The pressure is preferably from 1 to 100 bar, and a particularly preferred pressure is one which is equal to or larger than the autogenous pressure of the system at the particular temperature.

The reaction can moreover be carried out continuously or batchwise.

The reaction leads with high selectivity to the required, unsubstituted or substituted 1,1-diphenylethane. It is therefore possible to tolerate relatively high steady-state styrene concentrations in the reaction without the byproduct content becoming too high in the reaction. The steady-state styrene concentration in the reaction mixture is preferably not more than 5, particularly preferably not more than 2, in particular not more than 0.5, specifically not more than 0.1, % of the weight of the reaction mixture without catalyst.

In a preferred embodiment of the invention, the catalyst is mixed with the benzene, and the styrene is introduced in such a way that it is able continuously to react completely, and the steady-state styrene concentration does not exceed the maximum levels hereinbefore. Appropriate styrene concentrations can be adjusted by the rate of introduction, depending on the reaction temperature. In this batchwise procedure, the mixture of benzene and catalyst is brought to the reaction temperature, and then styrene is added. In place of styrene, it is also possible to meter in a styrene/benzene mixture, in which case the introduced styrene continuously reacts completely and thus its concentration remains low.

In the continuous procedure, preferably the catalyst is placed, with or without benzene, in a continuously operated stirred vessel or autoclave, and a styrene/benzene mixture is introduced in such a way that the steady-state styrene concentration does not exceed the maximum levels hereinbefore. It is once again possible for the concentration to be adjusted by the rate of introduction of styrene or styrene/benzene mixture. The stirred vessel is in this case equipped with an overflow with pressure maintenance valve. The catalyst is employed in the form of a suspension in benzene or of the shaped articles mentioned above. For starting up, the reactor is charged with benzene and brought to the reaction temperature. Then styrene or, preferably, a styrene/benzene mixture is metered in continuously in such a way that the low steady-state styrene concentration is set up. The reaction mixture leaving the overflow can be passed through a settler or a filter in order to remove the catalyst. The catalyst can also be incorporated in the form of shaped articles, so that removal is unnecessary.

It is furthermore possible for the catalyst to be employed as shaped articles in a reaction column, to introduce a styrene/benzene mixture continuously or batchwise, and to draw off the unsubstituted or substituted 1,1-diphenylethane formed from the bottom of the column. In this case, unreacted styrene/benzene mixture is taken off at the top of the column and can be returned to the column.

It is furthermore possible for the catalyst also to be placed in a fixed bed reactor, in particular tubular reactor, in which case more than 50, preferably more than 70, in particular more than 90, % by weight of the product discharge are returned to the reactor inlet for remixing. A large part of the product discharge is thus returned to dilute the precursor stream. A styrene/benzene mixture flows continuously through the tubular reactor.

The invention is illustrated in detail below by means of examples.

EXAMPLES

Preparation of the catalyst

Example 1

Solution 1: 5.1 g of $Al_2O_3$ (freshly precipitated $Al(OH)_3$ from $Al(NO_3)_3*8\ H_2O$ and 25% strength $NH_3/H_2O$) were dissolved in a solution of 9.6 g of NaOH and 80 g of water.

Solution 2: 12.8 g of crown ether 18-crown-6 (from Merck-Schuchardt) were dissolved in 75 g of silica sol (Ludox AS 40 from DuPont=40% $SiO_2$ in water).

Solution 1 and solution 2 were combined and stirred at room temperature for 10 minutes. This resulted in a gel, which was aged at room temperature for 3 days. The product was then induced to crystallize in an autoclave at 100° C. for 9 days and at 110° C. for 7 days. For workup, the product was filtered off, washed with water to neutrality, dried at 110° C. and then calcined at 550° C. for 20 h. The yield was 26 g. The product underwent exchange with 10% strength $NH_4Cl$ solution four times, was washed free of Cl, dried at 110° C. and calcined at 550° C. for 3 h.

The catalyst had a BET surface area of 701 m²/g, and the X-ray diffraction spectrum agreed with the spectrum of the ZSM-20 type. Elemental analysis showed 8.6% Al, 33.0% Si and 0.07% Na.

Example 2

13 g of catalyst from Example 1 were kneaded with 3.25 g of Pural® SB (supplied by Condea) and a solution of 0.25 g of formic acid in 19 g of water for 30 minutes. 2 mm extrudates were then produced from this composition and, after drying at 110° C., calcined at 500° C. for 16 h.

Example 3

Solution 1: 4.08 g of $Al_2O_3$ (freshly precipitated $Al(OH)_3$ from $Al(N_3)_3*8\ H_2O$ and 25% strength $NH_3/H_2O$) were dissolved in a solution of 7.68 g of NaOH and 80 g of water.

Solution 2: 10.24 g of 18-crown-6 were dissolved in 60 g of water and stirred with 24 g of Aerosil 200 (SiO2 from Degussa).

Solution 1 and solution 2 were combined and stirred at room temperature for 10 minutes. This resulted in a gel, which was aged at room temperature for 3 days. The product was then induced to crystallize in an autoclave at 120° C. for 16 days. For workup, the product was filtered off, washed with water until neutral, dried at 110° C. and then calcined at 550° C. for 20 h. The yield was 21 g. The product underwent exchange with 10% strength $NH_4Cl$ solution four times, was washed until free of Cl, dried at 110° C. and calcined at 550° C. for 3 h.

Procedure for the catalytic reactions

A gas chromatograph with a capillary column 30 m long (DB5, from J & W Scientific (Fisions), 0.1 $\mu$m) was used for analyzing the experiments which follow. (Temperature program: 5 minutes at 60° C., 10° C./minute to 300° C., 15 minutes at final temperature). Toluene was used as internal standard for quantification.

The 3 possible styrene dimers (identified by GC/MS) have been included in the following table. Their calibration factor was put equal to that of diphenylethane. The calibration factors for benzene (not listed), styrene and diphenylethane were determined by means of serial concentrations with toluene as internal standard.

Zeolites employed as comparative examples were of type H mordenite (PQ 900 H, from PQ), H-Y (from BASF), H-ZSM-5 (from Degussa) and H-beta-zeolite (Zeocat® PB, supplied by Uetikon).

Examples 4–9

1 g of the catalysts listed below and 10 ml of styrene/benzene solution were stirred at 50° C. for 3 h in a 50 ml compression glass vessel. The reaction product was then analyzed by GC.

TABLE 1

| | | Product composition | | | |
|---|---|---|---|---|---|
| No | Catalyst | Styrene | 1,1-Diphenyl-ethane | Dimers | Trimers | Yield |
| 4 | ZSM-5 | 2.26% | 0.0% | 2.42% | 0.05% | 0.0% |
| 5 | β-Zeolite | 0.0% | 1.77% | 4.85% | 0.2% | 10.1% |
| 6 | Mordenite | 0.0% | 1.59% | 3.27% | 0.1% | 6.1% |
| 7 | H-Y zeolite | 0.0% | 1.22% | 2.92% | 0.49% | 6.9% |
| 8 | Example 1 | 0.0% | 3.02% | 3.41% | 0.24% | 17.3% |
| 9 | Example 3 | 0.0% | 4.97% | 3.10% | 0.77% | 28.4% |

It is evident from the results in Table 1 that the catalysts according to the invention result in 1,1-diphenylethane with considerably higher yield and considerably better selectivity than the comparative catalysts. They are is superior to the zeolites known for this application.

Example 10 (continuous procedure)

12.4 g of catalyst from Example 2 were placed in a catalyst basket in an autoclave with a capacity of 50 ml. The autoclave was charged with benzene and heated to 200° C. Then a solution of 5% styrene in 95% benzene was continuously metered in at a rate of 120 ml/h. The overflow was discharged through a pressure maintenance valve (50 bar) and analyzed at regular intervals.

TABLE 2

| Running time [h] | Styrene | Diphenyl-ethane | Dimers | Trimers | Yield |
|---|---|---|---|---|---|
| 10 h | 0.13% | 7.3% | 0.04% | 0.30% | 81.8% |
| 18 h | 0.22% | 7.23% | 0.10% | 0.46% | 80.8% |
| 30 h | 0.64% | 5.56% | 0.64% | 0.31% | 59.5% |

We claim:

1. A process for preparing unsubstituted or substituted 1,1-diphenylethanes by catalytic reaction of benzene and styrene in the presence of a zeolite catalyst, wherein benzene and styrene each independently to have 1 to 5 substituents selected from the group consisting of halogen, $C_{1-10}$-alkyl, $C_{1-10}$-alkoxy, $C_{1-10}$-acyl, $C_{1-10}$-acyloxy or cyano, wherein the zeolite catalyst is selected from the group consisting of EMT or ZSM-20.

2. A process as claimed in claim 1, wherein the reaction is carried out at from −20° to 300° C. under from 1 to 100 bar.

3. A process as claimed in claim 1, wherein the steady-state styrene concentration in the reaction mixture is not more than 5% of the total weight of the reaction mixture.

4. A process as claimed in claim 1, wherein the benzene and styrene employed each independently have a maximum of one substituent on the aromatic nucleus, and the substituent in the styrene is located in the p position.

5. A process as claimed in claim 4, wherein unsubstituted benzene and unsubstituted styrene are reacted.

6. A process as claimed in claim 1, wherein the catalyst is mixed with the benzene, and the styrene is introduced in so that the steady-state styrene concentration is not more than 5% of the total weight of the reaction mixture.

7. A process as claimed in claim 1, wherein the catalyst is placed, with or without the benzene, in a continuously operated stirred vessel or autoclave, and styrene or a mixture of styrene and benzene is introduced in so that the steady-state styrene concentration is not more than 5% of the total weight of the reaction mixture.

8. A process as claimed in claim 1, wherein the catalyst is employed as shaped articles in a reaction column, a mixture of styrene and benzene is introduced continuously or batchwise, and the unsubstituted or substituted 1,1-diphenylethane formed is drawn off from the bottom of the column.

9. A process as claimed in claim 1, wherein the catalyst is placed in a fixed bed reactor and more than 50% by weight of the product discharge are returned to the reactor inlet for remixing.

* * * * *